(12) United States Patent
Kuo et al.

(10) Patent No.: US 10,694,939 B2
(45) Date of Patent: Jun. 30, 2020

(54) WHOLE EYE OPTICAL COHERENCE TOMOGRAPHY(OCT) IMAGING SYSTEMS AND RELATED METHODS

(71) Applicant: Duke University, Durham, NC (US)

(72) Inventors: Anthony Kuo, Durham, NC (US); Joseph Izatt, Durham, NC (US); Ryan McNabb, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/583,992

(22) Filed: May 1, 2017

(65) Prior Publication Data

US 2017/0311797 A1 Nov. 2, 2017

Related U.S. Application Data

(60) Provisional application No. 62/329,256, filed on Apr. 29, 2016.

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/117* (2013.01); *A61B 3/1233* (2013.01); *A61B 3/152* (2013.01)

(58) Field of Classification Search
CPC ..... A61B 3/102; A61B 5/0066; A61B 5/0073; A61B 5/7257; A61B 3/1225; A61B 5/0084; A61B 5/0059; A61B 5/02007; A61B 5/6852; A61B 3/12; A61B 3/14; A61B 3/1005; A61B 3/107; A61B 3/0025; A61B 1/07; A61B 3/1208; A61B 3/1241;
(Continued)

(56) References Cited

U.S. PATENT DOCUMENTS 5,040,229 A 8/1991 Lee et al.
5,493,109 A 2/1996 Wei et al.
(Continued)

FOREIGN PATENT DOCUMENTS

EP 1647370 A1 4/2006
KR 1020130000023 1/2013
(Continued)

OTHER PUBLICATIONS

Notice of Allowance received in U.S. Appl. No. 14/337,215 dated Dec. 23, 2015.
(Continued)

*Primary Examiner* — Brandi N Thomas
(74) *Attorney, Agent, or Firm* — Olive Law Group, PLLC

(57) ABSTRACT

Whole eye optical coherence tomography (OCT) imaging systems and related methods are disclosed. According to an aspect, an OCT imaging system includes a source having an associated source arm path. Further, the OCT imaging system includes a reference arm coupled to the source arm. Further, the OCT imaging system includes a sample arm having an associated sample arm path and coupled to the source arm. The sample arm includes at least one optical component configured to simultaneously scan both an anterior and posterior portion of an eye of a subject.

18 Claims, 7 Drawing Sheets

(51) Int. Cl.
  *A61B 3/117* (2006.01)
  *A61B 3/00* (2006.01)
  *A61B 3/15* (2006.01)
  *A61B 3/12* (2006.01)

(58) Field of Classification Search
  CPC .... A61B 3/125; A61B 5/0071; G02B 27/095;
   G02B 27/0955; G02B 27/0977; G02B
   27/0994; G02B 5/08; G02B 6/12021;
   G02B 6/262; G02B 6/32; G02B 6/4204;
   G02B 6/4206; G02B 6/4214; G02B 6/34;
   G02B 2006/12107; G02B 23/04; G02B
   23/2446; G02B 23/2469; G02B 27/283;
   G02B 5/3058
  USPC ........ 351/200, 203, 205, 206, 209–211, 221,
   351/222, 243–246
  See application file for complete search history.

(56) References Cited

U.S. PATENT DOCUMENTS

| | | | |
|---|---|---|---|
| 5,715,081 A | 2/1998 | Chastang et al. | |
| 5,963,301 A | 10/1999 | Volk | |
| 6,671,581 B2 | 12/2003 | Niemeyer et al. | |
| 7,791,794 B2 | 9/2010 | Reimer et al. | |
| 7,839,494 B2 | 11/2010 | Reimer et al. | |
| 7,907,166 B2 | 3/2011 | Lamprecht et al. | |
| 8,783,866 B2* | 7/2014 | Hart | A61B 3/102 351/205 |
| 9,207,638 B2 | 12/2015 | Dubois et al. | |
| 2001/0031078 A1 | 10/2001 | Doane | |
| 2002/0099290 A1 | 7/2002 | Haddad | |
| 2005/0270486 A1 | 12/2005 | Teiwes et al. | |
| 2006/0050991 A1 | 3/2006 | Jerebko et al. | |
| 2007/0086647 A1 | 4/2007 | Grady | |
| 2007/0263226 A1* | 11/2007 | Kurtz | A61B 5/0059 356/492 |
| 2007/0299309 A1 | 12/2007 | Seibel et al. | |
| 2008/0002183 A1 | 1/2008 | Yatagai et al. | |
| 2008/0019587 A1 | 1/2008 | Wilensky et al. | |
| 2008/0030497 A1 | 2/2008 | Hu et al. | |
| 2008/0058704 A1 | 3/2008 | Hee et al. | |
| 2008/0316430 A1* | 12/2008 | Hsu | G03B 21/28 353/20 |
| 2009/0018393 A1 | 1/2009 | Dick et al. | |
| 2009/0060332 A1 | 3/2009 | Knapp | |
| 2009/0131921 A1 | 5/2009 | Kurtz et al. | |
| 2009/0192523 A1 | 7/2009 | Larkin et al. | |
| 2009/0225407 A1 | 9/2009 | Nakayama et al. | |
| 2009/0244485 A1 | 10/2009 | Walsh et al. | |
| 2009/0257065 A1 | 10/2009 | Hauger et al. | |
| 2009/0287223 A1 | 11/2009 | Pua et al. | |
| 2010/0099076 A1* | 4/2010 | Mao | G01N 33/54313 435/5 |
| 2010/0202677 A1 | 8/2010 | Imamura et al. | |
| 2010/0228123 A1 | 9/2010 | Brennan et al. | |
| 2010/0331858 A1 | 12/2010 | Simaan et al. | |
| 2011/0032533 A1 | 2/2011 | Izatt et al. | |
| 2011/0043757 A1 | 2/2011 | Everett et al. | |
| 2011/0102802 A1* | 5/2011 | Izatt | A61B 3/102 356/479 |
| 2011/0122487 A1 | 5/2011 | Perelman et al. | |
| 2012/0092615 A1 | 4/2012 | Izatt et al. | |
| 2012/0184846 A1 | 7/2012 | Izatt et al. | |
| 2012/0188555 A1* | 7/2012 | Izatt | A61B 3/102 356/479 |
| 2012/0307205 A1 | 12/2012 | Zhou et al. | |
| 2013/0010259 A1 | 1/2013 | Carnevale | |
| 2013/0016319 A1 | 1/2013 | Vohnsen et al. | |
| 2013/0135584 A1 | 5/2013 | Alasaarela et al. | |
| 2013/0188140 A1 | 7/2013 | Bagherinia et al. | |
| 2013/0245375 A1 | 9/2013 | DiMaio et al. | |
| 2013/0293838 A1 | 11/2013 | Makihira et al. | |
| 2014/0009741 A1 | 1/2014 | Levien et al. | |
| 2014/0098345 A1* | 4/2014 | Cai | A61B 3/102 351/206 |
| 2014/0139916 A1 | 5/2014 | Doi et al. | |
| 2014/0142591 A1 | 5/2014 | Alvarez et al. | |
| 2014/0247425 A1 | 9/2014 | Hammer et al. | |
| 2014/0275760 A1 | 9/2014 | Lee et al. | |

FOREIGN PATENT DOCUMENTS

| | | |
|---|---|---|
| WO | 2005106786 A1 | 11/2005 |
| WO | 2012100030 A2 | 7/2012 |
| WO | 2012109301 A2 | 8/2012 |
| WO | 2013008033 A1 | 1/2013 |
| WO | 2013180773 A1 | 12/2013 |
| WO | 2014068058 A1 | 5/2014 |

OTHER PUBLICATIONS

Notice of Allowance received in U.S. Appl. No. 15/049,103 dated Oct. 10, 2016.
Office Action received in U.S. Appl. No. 14/337,215 dated May 12, 2015.
Office Action received in U.S. Appl. No. 14/337,215 dated Nov. 5, 2014.
Office Action received in U.S. Appl. No. 15/049,103 dated Jul. 5, 2016.
Otsu, A Threshold Selection Method from Gray-Level Histograms, IEEE Transactions on Systems, Man, and Cybemetics, vol. SMC-9, No. 1, Jan. 1979, U.S.
PCT International Search Report for PCT International Application No. PCT/US15/13870.
PCT International Written Opinion for PCT International Application No. PCT/US15/13870.
PCT Preliminary Report on Patentability and Written Opinion dated May 8, 2014 for related PCT International Application No. PCT/US2014/013243.
PCT Search Report and Written Opinion dated Jul. 13, 2012 for related application PCT/US2012/021839; iFD dated Jan. 19, 2012.
Perstein, M., Algorithms, Control Data Corp., Palo Alto, California.
Pircher, Michael et al., Simultaneous SLO/OCT Imaging of the Human Retina with Axial Eye Motion Correction, Optics Express, vol. 15, No. 25, Dec. 4, 2007.
Related application PCT/US2012/021839 filed Jan. 19, 2012 entitled System Enhancements for Ophthalmic Surgical Microscope Mounted Optical Coherence Tomography, not yet published.
Schulze, Jürgen P. et al.; "Visualization of Three-Dimensional Ultra-High Resolution OCT in Virtual Reality" Ophthalmology Department, Lariboisière Hospital, APHP, Paris, France.
SDI/BIOM: Still the Standard in Wide-Angle Viewing for All Microscope Models!, Insight Instruments, Inc., Stuart, Florida.
Shen, Liangbo et al.; "Novel Microscope-Integrated Stereoscopic Heads-up Display for Intrasurgical OCT in Ophthalmic Surgery", The Association for Research in Vision and Ophthalmology; Jun. 2015, vol. 56, 3514.
Shi et al., Normalized Cuts and Image Segmentation, IEEE Transactions on Pattern Analysis and Machine Intelligence, vol. 22, No. 8, Aug. 2000, U.S.
Shi, Minyan et al.; "A Stereo-Fluoroscopic Image-Guided Robotic Biopsy Scheme" IEEE Transactions on Control Systems Technology, vol. 10, No. 3, May 2002, pp. 309-317.
Stephanie J. Chiu, Cynthia A. Toth, Catherine Bowes Rickman, Joseph A. Izatt, and Sina Farsiu, "Automatic Segmentation of Cloaed-contour Features in Ophthalmic Images Using Graph Theory and Dynamic Programming", Published Apr. 26, 2012, Optical Society of America.
Takeda et al., Kernel Regression for Image Processing and Reconstruction, IEEE Transactions on Image Processing, vol. 16, No. 2, Feb. 2007, U.S.
The Age-Related Eye Disease Study Research Group, The Age-Related Eye Disease Study System for Classifying Age-Related Macular Degeneration From Stereoscopic Color Fundus Photographs: The Age-Related Eye Disease Study Report No. 6, Elsevier Service Inc., vol. 132, No. 5, 2001, U.S.

(56) References Cited

OTHER PUBLICATIONS

Tolliver et al., Unassisted Segmentation of Multiple Retinal Layers via Spectral Rounding, Presented in ARVO 2008 Annual Meeting, Fort Lauderdale, Florida, U.S., Apr. 2008.

U.S. Final Office Action for U.S. Appl. No. 14/337,215, dated May 12, 2015.

U.S. Non-Final Office Action for U.S. Appl. No. 13/010,448, dated Jan. 2, 2014.

U.S. Non-Final Office Action for U.S. Appl. No. 14/337,215, dated Nov. 5, 2014.

U.S. Non-Final Office Action for U.S. Appl. No. 15/049,103, dated Jul. 5, 2016.

U.S. Notice of Allowance for U.S. Appl. No. 13/014,48, dated May 13, 2013.

U.S. Notice of Allowance for U.S. Appl. No. 14/337,215, dated Jan. 11, 2016.

U.S. Notice of Allowance for U.S. Appl. No. 15/049,103, dated Oct. 24, 2016.

U.S. Office Action Response to Non-Final Office Action for U.S. Appl. No. 14/337,215, dated Apr. 6, 2015.

U.S. Office Action Response to Non-Final Office Action for U.S. Appl. No. 15/049,103, dated Oct. 6, 2016.

U.S. Response to Non-Final Office Action for U.S. Appl. No. 13/010,448, dated Mar. 31, 2014.

Viehland, Christian et al.; "Enhanced volumetric visualization for real time 4D intraoperative ophthalmic swept-source OCT" Biomedical Optics Express 1815, May 1, 2016 | vol. 7, No. 5 |.

Warshall, A Theorem on Boolean Matrices, Computer Associates, Inc., Woburn, Massachusetts, U.S.

Wieser, Wolfgang et al., Multi-Megahertz OCT: High Quality 3D Imaging at 20 Million A-Scans and 4_5 GVoxels Per Second, Optics Express, vol. 18, No. 14, Jun. 30, 2010.

Witte, S., Plaw;;ka, A., Ridder, M. C., van Berge, L., Mansvelder, H. D., & Groot, M. L. (2012). Short-coherence off-axis holographic phase microscopy of live cell dynamics. Biomedical Optics Express, 3(9), 2184-2189. http://doi.org/10.1364/BOE.3.002184.

Yazdanpanah et al., Segmentation of Intra-Retinal Layers from Optical Coherence Tomography Images Using an Active Contour Approach, IEEE, 2010, U.S.

"American National Standard for Safe Use of Lasers" American National Standards Institute, Inc. Mar. 16, 2007.

Aschke et a l., "Augmented Reality in Operating Microscopes for Neurosurgical Interventions." IEEE, Mar. 22, 2003, pp. 652-654 (Mar. 22, 2003), p. 652, col. 2; p. 653, col. 2-p. 653, col. 1; Fig 3 [online].

Goncharov, Alexander V. et al.; "Wide-field schematic eye models with gradient-index lens" J. Opt. Soc. Am. A., vol. 24, No. 8/Aug. 2007, pp. 2157-2174.

Bellman, On a Routing Problem, Richard Bellman, vol. XVI, No. 1, The RAND Corporation, pp. 87-90, 1957, U.S.

Bichlmeier, Christoph et al.; "The Tangible Virtual Mirror: New Visualization Paradigm for Navigated Surgery" Chair for Computer Aided Medical Procedures (CAMP), TU Munich, Germany.

Dabov, Kostadin et al., Image Denoising by Sparse 3-D Transform-Domain Collaborative Filtering, IEEE Transactions on Image Processing, vol. 16, No. 8, Aug. 2007.

Dhalla, Al-Hafeez et al., Complex Conjugate Resolved Heterodyne Swept Source Optical Coherence Tomograph) Using Coherenece Revival, Biomedical Optics Express, vol. 3, No. 3, Feb. 24, 2012.

Dijkstra, A Note on Two Problems in Connexion with Graphs, Cambridge University Press, 1897, vol. 13, p. 26-8, U.K.

International Search Report and Written Opinion dated Aug. 16, 2016 from International Application No. PCT/US16/28862.

International Search Report and Written Opinion dated Aug. 12, 2016 from International Application No. PCT/US16/3105.

Elias, P., et al., A Note on the Maximum Flow Through a Network, IRE Transactions on Information Theory, 1956, pp. 117-119.

Fabritius et al., Automated Segmentation of the Macular by Optical Coherence Tomography, Optics Express, vol. 17, No. 18, Aug. 31, 2009, US.

Farsiu et al., Fast Detection and Segmentation of Drusen in Retinal Optical Coherence Tomography Images, Ophthalmic Technologies XVIII, Proc. of SPIE vol. 6844, 2008, U.S.

Ferguson, R. Deniel et aL, Tracking Optical Coherence Tomography, Optics Letters, vol. 29, No. 18, Sep. 15, 2004.

Fernandez et al, Automated Detection of Retinal Layer Structures on Optical Coherence Tomography Images, Optics Express, vol. 13, No. 25, Dec. 12, 2005, U.S.

Final Rejection received in U.S. Appl. No. 13/353,612 dated May 10, 2017 (eleven (11) pages).

Garvin et al., Automated 3-D Intraretinal Layer Segmentation of Macular Spectral-Domain Optical Coherence Tomography Images, IEEE Transactions on Medical Imaging, vol. 28, No. 9, Sep. 2009, U.S.

Garvin, M.K., et al., Intraretinal Layer Segmentation-Search, IEEE, 0278-0062, pp. 1495-1505, 2008.

Graph cuts segmentation—medical images, Jacquot et al., I EEE,978-0-7695-3122, 2008, pp. 631-635.

Haeker et al., Automated Segmentation of Intraretinal Layers from Macular Optical Coherence Tomography Images, Society of Photo-Optical Instrumentation Engineers, 2007, U.S.

Hendargo, Hansford C. et al., Automated Non-Rigid Registration and Mosaicing for Robust Imaging of Distinct Retinal Capillary Beds Using Speckle Variance Optical Coherence Tomography, Biomedical Optics Express, vol. 4, No. 6, May 7, 2013.

International Search Report and Written Opinion issued in PCT Application No. PCT/US2016/016900 dated May 5, 2016.

International Preliminary Report on Patentability dated Jul. 23, 2013 for corresponding application PCT/US2012/021839 (filed Jan. 19, 2012).

Jung, Woonggyu et al.; "Handheld Optical Coherence Tomography Scanner for Primary Care Diagnostics" IEEE Transactions on Biomedical Engineering, vol. 58, No. 3, Mar. 2011. pp. 741-744.

International Search Report and Written Opinion dated Jan. 5, 2017 from International Application No. PCT/US16/51360.

International Search Report and Written Opinion dated May 19, 2016 from related International Application No. PCT/US16/16830.

Intra-retinal segmentation—images, Mishra et al., Optic Express 23719, Published Dec. 11, 2009, pp. 1-10.

Ishikawa et al., Macular Segmentation with Optical Coherence Tomography, Investigative Ophthalmology & Visual Science, vol. 46, No. 6, Association for Research in Vision and Ophthalmology, Jun. 2005, U.S.

Jaquot, J.Z., et al.,Graph Cuts Segmentation-Medical Images, IEEE, pp. 631-635. 2008.

Ji, Na et al., Adaptive Optics Via Pupil Segmentation for High-Resolution Imaging in Biological Tissues, Nature Methods, vol. 7, No. 2, Feb. 2010.

Kavraki, Lydia E. et al.; "Probabilistic Roadmaps for Path Planning in High-Dimensional Configuration Spaces" IEEE Transactions on Robotics and Automation, vol. 12, No. 4, Aug. 1996.

Koreeda, Y. et al.; "Development and testing of an endoscopic pseudo-viewpoint alternating system" Int J CARS, Jun. 21, 2014.

Kozak, Igor et al.; "Virtual reality simulator for vitreoretinal surgery using integrated OCT data" Clinical Ophthalmology 2014:8 pp. 669-672.

Larocca et al., "Optimization of confocal scanning laser opthalmoscope design." Journal of Biomedical Optics. Jul. 2013 {Jul. 2013). pp. 076015-1-076015-2, 076015-8 [online].

LaRocca, Francesco et al.; "Handheld simultaneous scanning laser ophthalmoscopy and optical coherence tomography system" Biomedical Optics Express, Nov. 1, 2013 | vol. 4, No. 11, pp. 2307-2321.

LaValle, Steven M. et al.; "Rapidly-Exploring Random Trees: A New Tool for Path Planning" Department of Computer Science, Iowa State University.

Lee, K., et al. Segmentation of the Optic Disc in 3-D OCT Scans of the Optic Nerve Head. IEEE Transactions on Imaging Imaging, vol. 29(1): pp. 159-168, Jan. 2010.

Liao, Wen-Hung et al., Robust Pupil Detection for Gaze-Based User Interface, EGIHMI, Feb. 7, 2010.

(56) References Cited

OTHER PUBLICATIONS

Kelly, John P. et al.; "Imaging a Child's Fundus Without Dilation Using a Handheld Confocal Scanning Laser Ophthalmoscope" Arch Ophthalmol/vol. 121, Mar. 2003, pp. 391-396.

Lu et al., Automated Layer Segmentation of Optical Coherence Tomography Images, IEEE Transactions on Biomedical Engineering, vol. 57, No. 10, Oct. 2010, U.S.

Lu, Chen D.; "Handheld ultrahigh speed swept source optical coherence tomography instrument using a MEMS scanning mirror" Biomedical Optics Express, Jan. 1, 2014 | vol. 5, No. 1, pp. 293-311.

Lujan, Brandon J., et al., Revealing Henle's Fiber Layer Using Spectral Domain Optical Coherence Tomography, Investigative Ophthalmology & Visual Science, Mar. 2011, vol. 52, No. 3, 2011.

Martinez-Conde, Susan et al., The Role of Fixational Eye Movements in Visual Perception, Nature Reviews, Neuroscience, vol. 5, pp. 229-240, Mar. 2004.

McNabb, Ryan P_ et al., Distributed Scanning Volumetric SDOCT for Motion Corrected Corneal Biometry, Biomedical Optics Express, vol. 3, No. 9, Aug. 10, 2012.

Scott, Adrienne W. et al.; "Imaging the Infant Retina with a Hand-held Spectral-Domain Optical Coherence Tomography Device" Infant Retina Imaging by Hand-Held SD OCT, vol. 147, No. 2, pp. 364-373.

Mishra, A., et al., Intra-Retinal Segmentatioin-Images, Optic Express 23719, pp. 1-10, Dec. 11, 2009.

Thevenaz, Philippe et al.; "User-Friendly Semiautomated Assembly of Accurate Image Mosaics in Microscopy" Microscopy Research and Technique vol. 70: pp. 135-146 (2007).

Niemeijer et al., Vessel Segmentation in 3D Spectral OCT Scans of the Retina, Medical Imaging 2008, Image Processing, Proc. of SPIE, vol. 6914, 2008, U.S.

Non-Final Office Action received in U.S. Appl. No. 13/010,448 dated Jan. 2, 2014.

Notice of Allowance received in U.S. Appl. No. 13/010,448 dated May 13, 2014.

\* cited by examiner

WHOLE EYE OPTICAL COHERENCE TOMOGRAPHY(OCT) IMAGING SYSTEMS AND RELATED METHODS

CROSS REFERENCE TO RELATED APPLICATION

This application claims the benefit of and priority to U.S. Provisional Patent Application No. 62/329,256, filed Apr. 29, 2016 and titled WHOLE EYE OPTICAL COHERENCE TOMOGRAPHY SCANNER AND METHODS OF USING SAME, the disclosure of which is incorporated herein by reference in its entirety.

STATEMENT AS TO FEDERALLY SPONSORED RESEARCH

This invention was made with the support of the U.S. government under Federal Grant No. R01EY024312 awarded by the National Institutes of Health (NIH). The government has certain rights in the invention.

TECHNICAL FIELD

The presently disclosed subject matter relates to optical coherence tomography (OCT). Particularly, the presently disclosed subject matter relates to whole eye OCT imaging system and related methods.

BACKGROUND

OCT is an interferometric, optical imaging technique that provides three-dimensional information utilizing backscattered light from an interrogated sample such as biological tissue. OCT imaging systems typically include five main components: a light source, an interferometer, a reference arm, a sample arm, and a detector. An OCT imaging system may acquire an image by utilizing a broad bandwidth low-temporal coherence light source with an interferometer, changing the path length difference between the reference and sample arms by moving a reference arm mirror, and subsequently recording the intensity of the resulting fringes at a photo-receiver. This technique is referred to as time domain OCT (TD-OCT). Later, it was shown that by fixing the reference mirror and recording the spectrum of illuminating wavelengths an image with improved signal-to-noise ratio (SNR) may be acquired by taking a Fourier transform of the spectrum. This can be achieved by one of two ways. Spectral domain OCT (SD-OCT) utilizes the same source type as TD-OCT but swaps the photo-receiver for a spectrometer, separating wavelengths onto the pixels of a camera. Swept source OCT (SS-OCT) (also referred to as optical frequency domain imaging or OFDI) changes the light source such that the source nominally provides a single output wavelength at a given instant and is swept over a range of wavelengths. A photo-receiver records the intensity of the detected light as the wavelengths are swept over time.

OCT imaging systems have been used in a variety of medical fields. For example, OCT imaging systems have been used for scanning eyes. Current commercial OCT system sample arms only scan one portion of the eye well (anterior eye only or posterior eye only). A few research OCT imaging systems have been described to image both the anterior and posterior eye, but to date, these have limited fields of view due to inherent limitations in available optical components and design. There is a desire to provide OCT imaging systems with improved fields of view in order to provide a whole eye OCT image.

BRIEF SUMMARY

Disclosed herein are whole eye OCT systems and related methods. Particularly, a system as disclosed herein may be a scanner suitable for "whole eye" scanning of an eye of a subject. An aspect of the present disclosure provides an OCT sample arm that enables wide field scans of both the anterior and posterior eye simultaneously to create "whole eye" scanning of an eye of a subject in a relatively compact footprint. The scanner may include optics to ensure focused light across the wide scan range for both the anterior and posterior eye. The system may provide for independent focus control for the posterior eye to compensate for refractive error in the subject's eye without affecting the focus of the simultaneous scanning anterior eye channel. Further, a system may include wire-grid polarizing cube beam-splitters to enable polarization selectivity over a large scan range, thereby enabling polarization encoding and discrimination of the anterior and posterior eye channels over a large field of view.

Whole eye optical coherence tomography (OCT) imaging systems and related methods are disclosed. According to an aspect, an OCT imaging system includes a source having an associated source arm path. Further, the OCT imaging system includes a reference arm coupled to the source arm. Further, the OCT imaging system includes a sample arm having an associated sample arm path and coupled to the source arm. The sample arm includes at least one optical component configured to simultaneously scan both an anterior and posterior portion of an eye of a subject.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Unless otherwise defined, all technical terms used herein have the same meaning as commonly understood by one of ordinary skill in the art to which this disclosure belongs.

Articles "a" and "an" are used herein to refer to one or to more than one (i.e. at least one) of the grammatical object of the article. By way of example, "an element" means at least one element and can include more than one element.

The present disclosure provides OCT imaging systems having a sample arm capable of scanning wide fields of view (FOV). Particularly, the sample arm may scan both the human ocular anterior segment (i.e., cornea, iris, and lens) as well as the posterior eye (i.e., retina, choroid, and sclera) simultaneously. The sample arm may couple with a single extended depth OCT engine, such as coherence revival or VCSEL based engines. Sample arms in accordance with embodiments of the present disclosure are capable of scanning both the anterior and posterior eye simultaneously with wide FOV enabling human "whole eye" scanning. OCT imaging systems incorporating scanner in accordance with embodiments of the present disclosure are described in more detail in the text and figures below.

Figure 1:
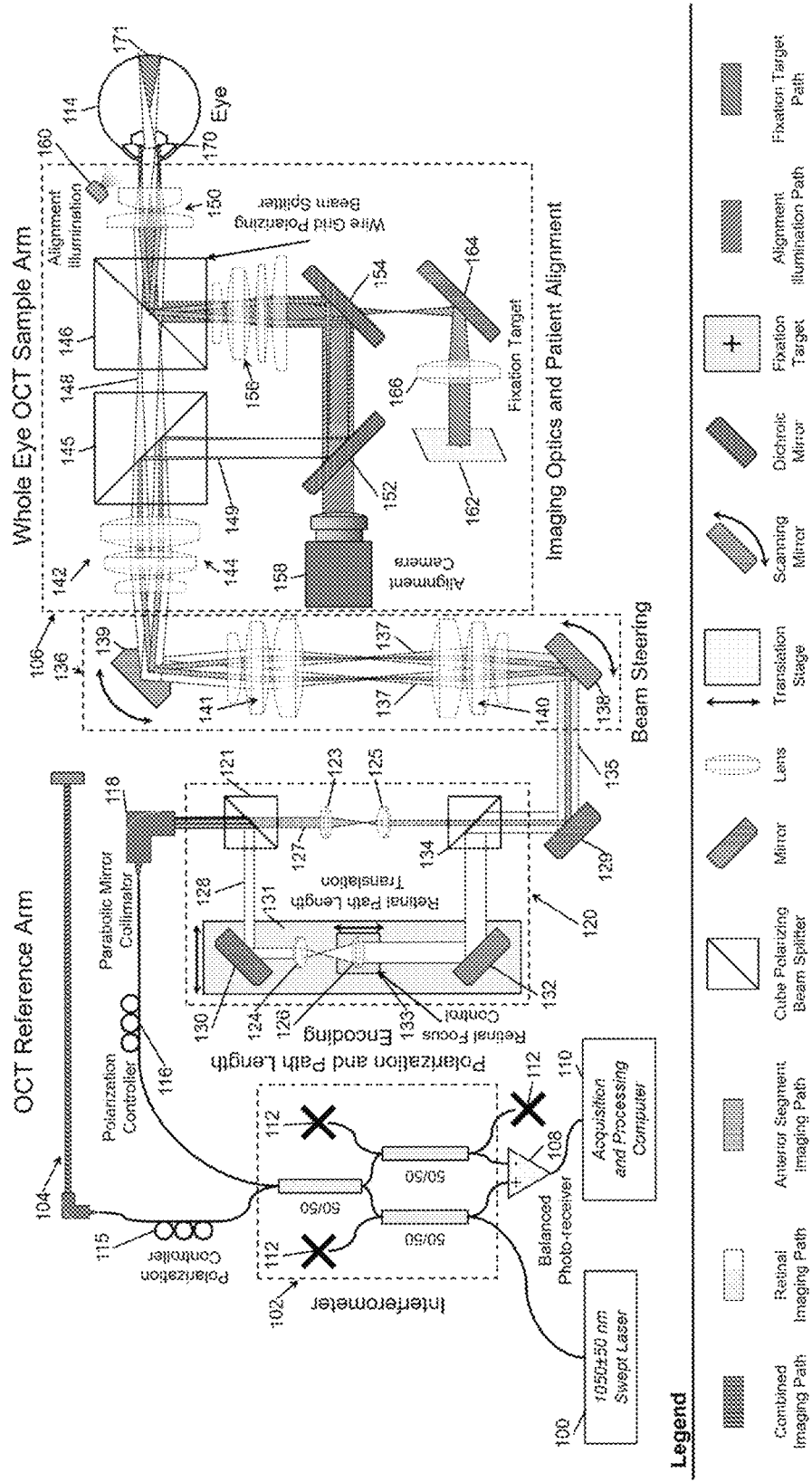
FIG. 1 is a schematic diagram of a wide-field whole eye OCT imaging system in accordance with embodiments of the present disclosure.

FIG. 1 is a schematic diagram of a wide-field whole eye OCT imaging system in accordance with embodiments of the present disclosure. Referring to FIG. 1, the system utilizes and includes an SS-OCT system including a swept laser source 100, a fiber-based spectrally balanced interferometer 102, a reflective, stationary reference arm 104, a sample arm 106, a photo-receiver 108, and a single acquisition and processing computer 110. Although a particular SS-OCT system is described in this example, it is noted that any other suitable SS-OCT system may be utilized. Further, in other embodiments, a suitable TD-OCT system may be used in place of an SS-OCT system.

In accordance with embodiments, the swept laser source 100 has a central wavelength of 1050 nm, a bandwidth of 100 nm, and a sweep rate of 200 kHz. It is noted that any other suitable light source may be utilized that has a suitable sweep rate at a desired central wavelength and bandwidth. Further, it is noted that the whole eye OCT sample arm 106 may be suitably altered to work with different imaging wavelengths, bandwidths, and sweep rates by use of different lenses and/or beam splitters that are configured for desired working wavelengths. In the cases of either a time domain or spectral domain OCT system, the light source may be changed to a low temporal coherence light source including but not limited to a superluminescent diode, femtosecond laser, supercontinuum laser, white light source, or any other suitable light source.

The system may be used to acquire repeated B-scans such that the fovea, optic nerve head, and anterior chamber were observed within each B-scan. Each B-scan consisted of 1200 A-scans with each A-scan consisting of 4128 samples or 11.1 mm of depth. The retina was encoded into the first 3 mm of the scan with the anterior chamber occupying the remainder.

In accordance with embodiments, the interferometer 102 is a single mode fiber-based spectrally balanced Michelson interferometer utilizing three fused fiber couplers that split an input into two outputs evenly with 50% of light going to one port and 50% of light going to another. It is noted that any other suitable fiber-based interferometer topologies may be utilized. Alternatively, a free space interferometer may be utilized with the whole eye OCT based sample arm 106. In this example, the interferometer has multiple, unused ports 112 that can be used for additional applications such as, but not limited to, optical power monitoring, start of sweep trigger generation, or a linear in wavenumber clock for the source output sweep. Further, for example, polarization maintaining single-mode fiber may be used throughout the interferometer.

In accordance with embodiments, the reference arm 104 may be a reflective reference arm with light reflected off a single mirror and back coupled into a fiber. Alternatively, a transmissive reference arm may be used. Polarization of the light within the reference arm 104 may be controlled by adjusting the stress-induced birefringence present within the optical fiber through the use of spooled fiber on a multi-paddle controller. Polarization may be controlled through the use of and not limited to a half-wave plate, quarter-wave plate or any suitable form of phase retarder. While a single mirror is utilized in the example of FIG. 1, the reference arm may be split into two paths, one for each polarization. By splitting into two paths, independent optical path length control can be provided for each.

In accordance with embodiments, the photo-receiver 108 is a balanced photo-receiver configured for signal detection. Alternatively, the photo-receiver may be a single or unbalanced photo-receiver; however, there may be degradation of SNR. In other embodiments, a spectrometer may be used along with a SD-OCT system. In embodiments in which the sample arm is based on polarization splitting, a polarization diversity detection scheme utilizing two balanced photo-receivers may be utilized.

Figure 2:
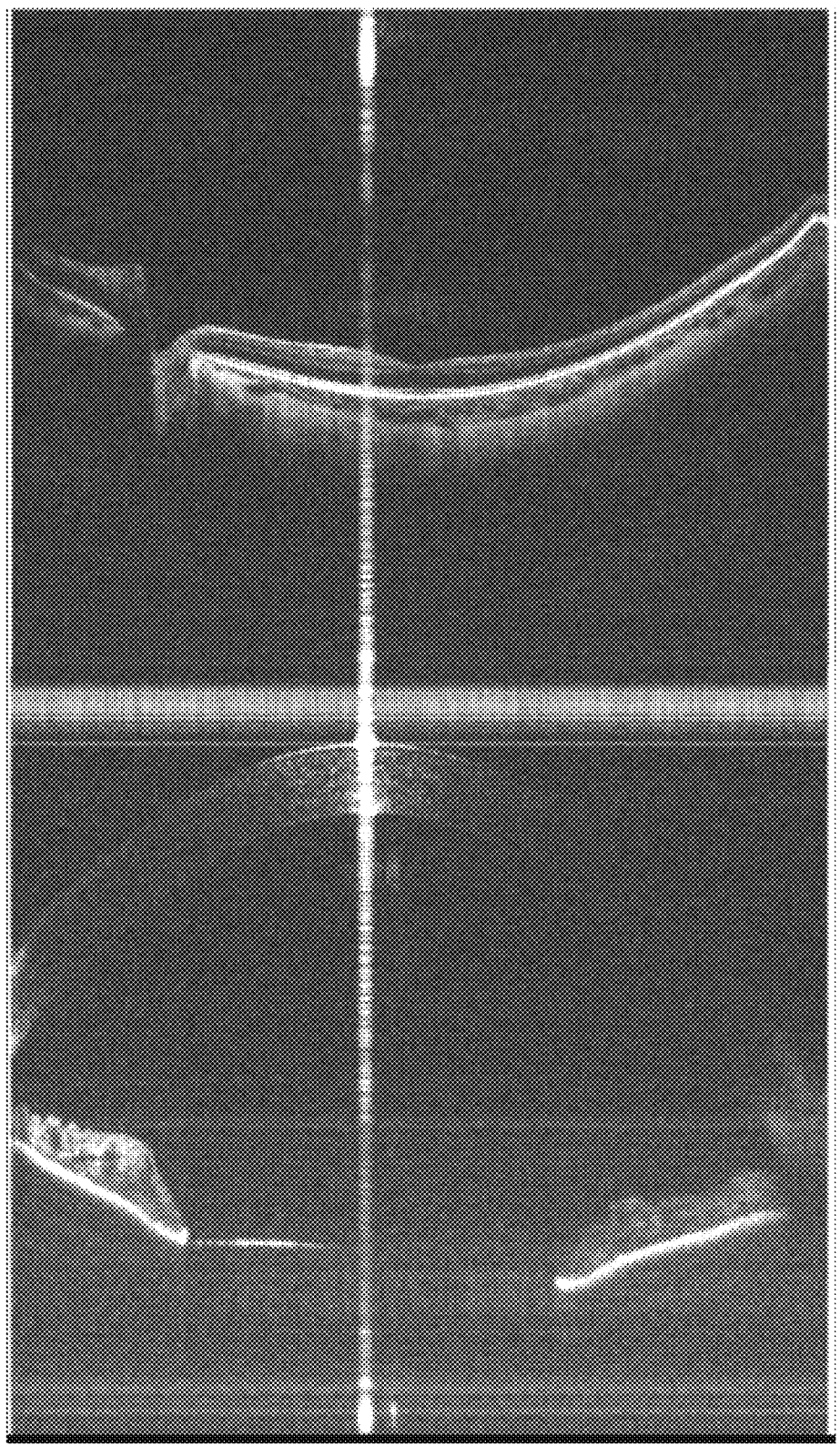
FIG. 2 is an image of a whole eye OCT image of a retina shown in the top portion and an anterior segment shown in the bottom portion.

In accordance with embodiments, the sample arm 106 implements polarization splitting to provide two separate imaging channels for an eye 114 under observation. One imaging channel is for the ocular anterior segment. The other imaging channel is for the retina where each channel is depth encoded into the OCT image. For example, FIG. 2 is an image of a whole eye OCT image of a retina shown in the top portion and an anterior segment shown in the bottom portion. Light polarization exiting the fiber may be controlled through the use of a spooled fiber, multi-paddle polarization controller 116. In example, polarization can be controlled through the use of, but not limited to, a half-wave plate, quarter-wave plate, or any form of phase retarder. A reflective off-axis parabolic mirror collimator 118 may generate a collimated or pencil beam from the output of the fiber. A refractive or diffractive collimator may be utilized in place of the reflective collimator.

Following the collimator 118, three sequential sub-systems may be utilized: polarization and path length encoding (block 120), beam steering (block 136), and imaging optics and patient alignment (block 106). The sub-systems in this example are contained within block 120. The polarization and path length encoding sub-system can introduce a path length difference, where beam 127 follows a shorter path than beam 128, between the two orthogonal linear polarizations present within the collimated beam and condition each polarization for its intended image plane. The system can be constructed such that beam 127 may follow a longer optical path than 128 or follow a path of equal distance. Following the collimator 118, the beam passes through a dielectric polarization splitting cube beam splitter 121 that splits the collimated beam into two collimated beams: one 127 with a P-polarization (or vertical polarization), and the other 128 with S-polarization (or horizontal polarization). In an example, all beam splitters throughout the sample arm 106 can be replaced with wire grid based beam splitters and may be of the aforementioned cube variety or be in a plate geometry. Here the P-polarized light is destined for the ocular anterior segment (see beam 149). Following that path, the light encounters a beam shrinking telescope (lenses 123 and 125) to condition the beam to have the correct spot size at the anterior segment image plane. We utilized two achromatic lenses 123 and 125 with positive but different focal lengths placed a fixed distance apart such that it equals the sum of their focal lengths. Here lens 123 has a longer focal length than lens 125. A similar result could be achieved with other refractive, diffractive or reflective configurations. Additionally, an iris may be used to cut beam diameter with a loss of optical power. In this example, a beam shrinking telescope is used, but it should be understood that other telescopes such as a beam expanding telescope may be used, or no telescope may be used. Following the telescope, the P-polarized beam is again collimated with a smaller diameter and then encounters a second polarizing beam-splitter cube 134 oriented such that the P-polarized light pass through leaving the sub-system. The path length of the P-polarized light in our system is fixed but may be adjusted such that it may be translated to provide the ability to tune the path length.

Returning to polarizing beam splitter cube 121, light 128 that is S-polarized is reflected off the dielectric interface within the cube 121 and is destined for the retina (light beam 148). The collimated S-polarized light 128 from the cube 121 reflects off a fold mirror 130, passes through two lenses 124 and 126 functioning as a beam expander, reflects off a second fold mirror 132, and reflects off the dielectric interface of another beam splitter cube 134 and becomes coaxial with the P-polarized light but having undergone a different optical path length. This difference is due to the distance through the two fold mirrors from the two beam splitters. This path difference may be electronically controlled by mounting the fold mirrors 130 and 132 onto a motorized stage 131 but may also be placed on a manually controlled stage. This path length difference is used for tuning the system and correcting for the length of the subject's eye 114. Other geometries may be utilized for controlling the path length such as, for example, by using a dove prism in place of the mirrors. The beam-expander may alternatively be suitably positioned either before or after. For the beam expander, we utilized two achromatic lenses 124 and 126 with positive but different focal lengths placed a fixed distance apart such that it equals the sum of their focal lengths. Here lens 126 has a longer focal length than lens 124. The beam expander can serve two purposes: increase the beam diameter to have the desired spot size at the retina; and by placing one lens (either 124 or 126) on a translation stage 133 and changing the distance between lenses 124 and 126. Diopter or focus control can be provided at the retina without modifying the anterior segment beam. The second purpose can eliminate the need for the subject to wear glasses or other corrective optics. The distance between the two lenses can be electronically controlled through a motorized stage 133, but the distance may also be manually controlled. The beam expander may be replaced with other refractive, diffractive, or reflective configurations. Diopter control can be achieved in other ways as well such as adding/replacing one of the beam expander lenses with a tunable lens or utilizing a deformable mirror. After the second beam splitter, the S-polarized and P-polarized beams may be coaxial 135 and may be directed to the beam steering sub-system 136 with a fold mirror 129 to reduce the system footprint.

Beam steering is utilized to change the angle of the collimated S- and P-polarized beams 137 relative to the overall optical axis. Two orthogonal mirrors mounted on galvanometers 138 and 139 can be utilized where one mirror was imaged onto the other through the use of a one-to-one 4-F refractive telescope consisting of lens groups 140 and 141. We utilized identical two achromatic triplet lens groups with identical focal lengths placed a fixed distance apart such that it equals the sum of their focal lengths. Lens group 140 was placed one focal length away from scanning mirror 138 and scanning mirror 139 was placed one focal length away from lens group 141. By changing the position of the mirrors the beams are simultaneously deflected and with the imaging optics are focused at different points at each beam's respective image plane. By scanning both mirrors over a range of deflection angles we can build up an image over the space of the image plane. The telescope could have been replaced by any other optical configuration that images one galvanometer mirror on to the other. Other methods that provide two dimensional beam steering could have been used including utilizing offset orthogonal galvanometers (thus omitting the telescope) or a 2D scanning mirror such as one based off a MEMS device or voice-coils. The orientation of the mirrors and the entire sub-system is such that the light undergoes a 90° rotation such when the light enters the imaging optics the anterior segment beam rotates from P-polarized to S-polarized and the retina beam rotates from S-polarized to P-polarized. A wave plate or other polarization rotating optical device may be used to achieve the same effect.

In accordance with embodiments, components for imaging and patient alignment are within block 106. The imaging optics take the output of the beam scanning sub-system 136 and focus the collimated beams at two separate image planes, one (148, P-polarized) at the retina 171 and one (149, S-polarized) at the anterior segment 170. The retinal path includes a 4-F telescope, generally designated 142, that images the second galvanometer mirror to the pupil of the subject's eye. The 4-F telescope 142 includes cube beam splitters 145 and 146 positioned between the two lens groups, generally designated 144 and 150. The first lens group 147 can create a telecentric image plane (i.e., an image plane with no curvature and incident beams are normal to the plane) one focal length away. For lens group 144, an air-spaced achromatic Cooke triplet design having two lenses made from crown glass and the middle lens made from flint glass may be used. Other suitable lens designs may be utilized in place of 144. The first cube beam splitter 145 may be a dielectric polarizing cube beam splitter that transmits P-polarized light and reflects S-polarized light at the dielectric interface. The acceptance angles of light incident to the dielectric polarizing cube beam splitters are limited to a small range (±2.5°) around normal. The first lens group 144 may have a telecentric image plane. The second polarizing beam splitter 146 may include two right angle prisms and a glass plate sandwiched between the two prisms along the hypotenuse. The glass plate has a wire grid polarizer deposited on its surface. An example advantage of a wire grid polarizer is that it allows for much larger range of input acceptance angles. While this is not utilized for the retinal imaging path, it is critical to the anterior segment path. The wire grid polarizer cube may be replaced by a suitable plate. The right angle prisms may have its corners removed that are closest to the imaging subject for reducing interference of the imaging device with the subject's face.

The second lens group 150 of the 4-F telescope 142 can complete the imaging of the second galvanometer mirror to the subject's ocular pupil. For lens group 150, an air-spaced achromatic doublet design with one lens made from crown glass and the other lens made from flint glass may be used.

Other suitable lens designs may be utilized in place of lens group 150. The second lens group 150 may be tapered to again reduce interference with the subject. P-polarized light leaving the second lens group 150 can be collimated assuming the Diopter control of the polarization and path length encoding sub-system of block 120 is in its nominal position. The optics of the subject's eye focus the collimated light to the retina 138.

Figure 3:
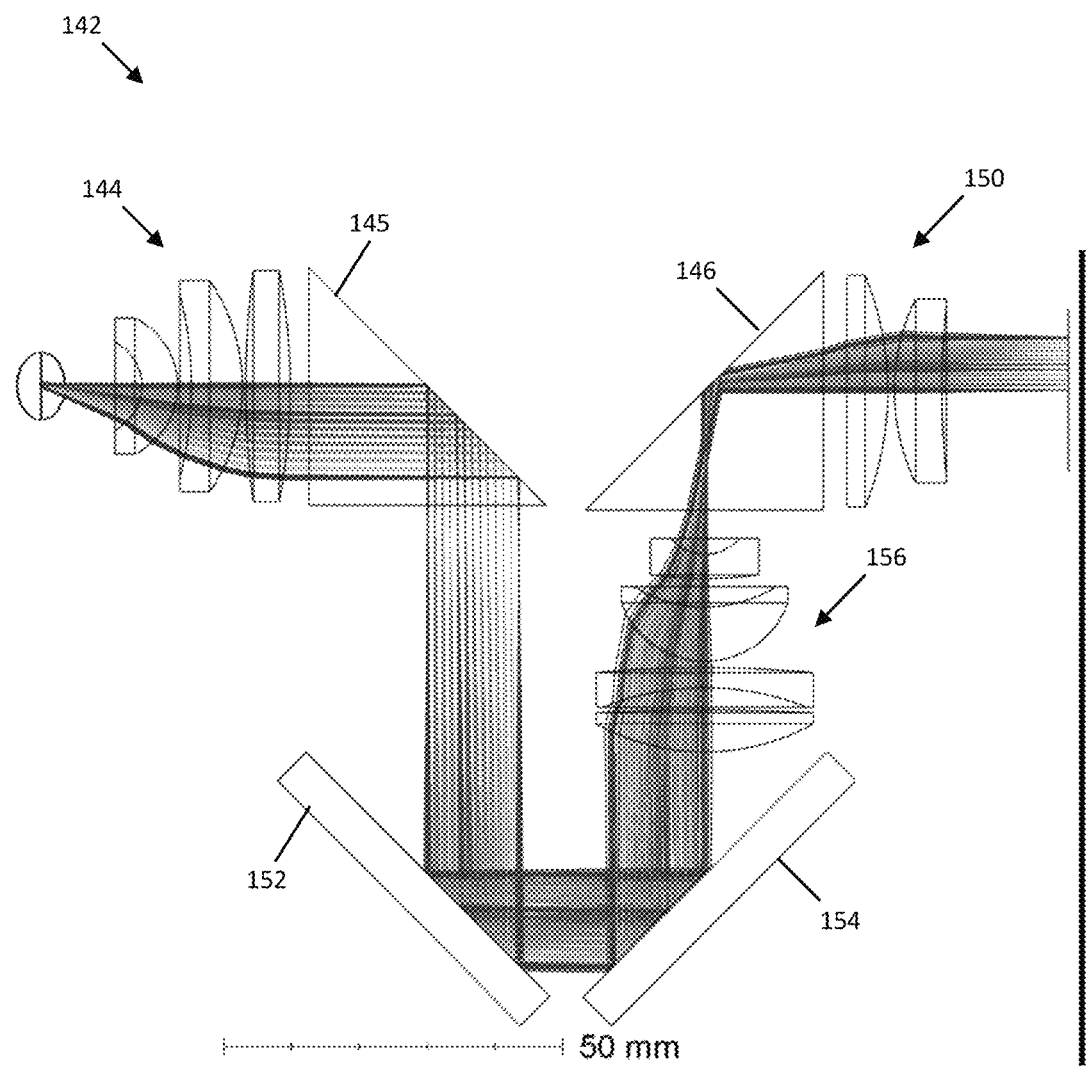
FIG. 3 is a beam steering ray diagram utilizing orthogonal scanning mirrors and a 1:1 4-F in accordance with embodiments of the present disclosure.

The light for the anterior segment utilizes the same optics of the retinal light path, but because the light is S-polarized light it is reflected at the hypotenuses of both polarizing beam splitter cubes (see FIG. 3). S-polarized light is focused by the first lens group 148 just as the P-polarized light. The light is reflected 90° by the beam splitter cube 145 and with a telecentric image plane a focal distance away from the first lens group 144. By utilizing a pair of fold mirrors 152 and 154 the light is steered back to the second, wire grid polarizing beam splitter 146. A third lens group 156 may be placed between the second fold mirror 154 and the second beam splitter 146. As a result, a 4-F telescope is formed with the second lens group 150 such that it images the telecentric image plane of the first lens group 144 to create a telecentric image plane at the anterior segment 170 of the subject's eye 114. For lens group 156, two air-spaced achromatic doublets may be used where in each doublet one lens was made from crown glass and the other lens made from flint glass giving two lenses made of crown glass and two lenses made of flint glass. Other suitable lens designs may be utilized in place of lens group 156. The third lens group 156 may be split or designed such that it may be placed anywhere in this fold space between the two polarizing beam splitters 145 and 146. By utilizing a wire grid polarizing beam splitter for the second splitter 146, the system can have large input angles into the splitter and allow for a large field of view at the anterior segment 170. Another topology that images both the anterior segment and retina simultaneously places the second beam splitter after the second lens group and can benefit from a wire grid polarizer to generate a larger field of view on the retina. Such a topology may have an additional lens group, and the addition of a beam splitter following lens groups two and four sets a fundamental working distance from the patient due to imaging through the glass of the beam splitter.

The fold mirrors 152 and 154 within the anterior segment path may be dichroic mirrors or any other suitable mirrors (e.g., metal or dielectric mirrors) that transmit shorter wavelengths of light and reflect light at the system's imaging wavelengths. This can allow for inclusion of additional accessories for patient alignment. The first fold mirror 152 can allow for a camera 158 that images the subject's iris. The illumination for the camera 158 can come from LEDs 160 that are aimed obliquely to the subject's cornea outside the OCT imaging axis. Illumination may also come from ambient light or from light that is coaxial with the camera 158 and the rest of the imaging system. Instead of an iris camera, a camera that images the retina or fundus may be utilized.

A fixation target 162 can allow the subject to look at a constant point, and the fixation target 162 may be placed behind the second dichroic mirror 154. A suitable mirror 164 and lens 166 may be suitably positioned and used with the fixation target 162. An OLED screen may be used that allows for multiple colors and dynamic changes to the fixation target 162. Other versions of the target may come from LCD screens, LEDs or any other static or dynamic visible light source that the patient can easily fixate on. Neither of these are required for operation but can make imaging easier and both can be placed external to the OCT imaging path. It is noted that in this example each was placed in its own channel but both may be placed behind a single dichroic mirror.

Figure 4:
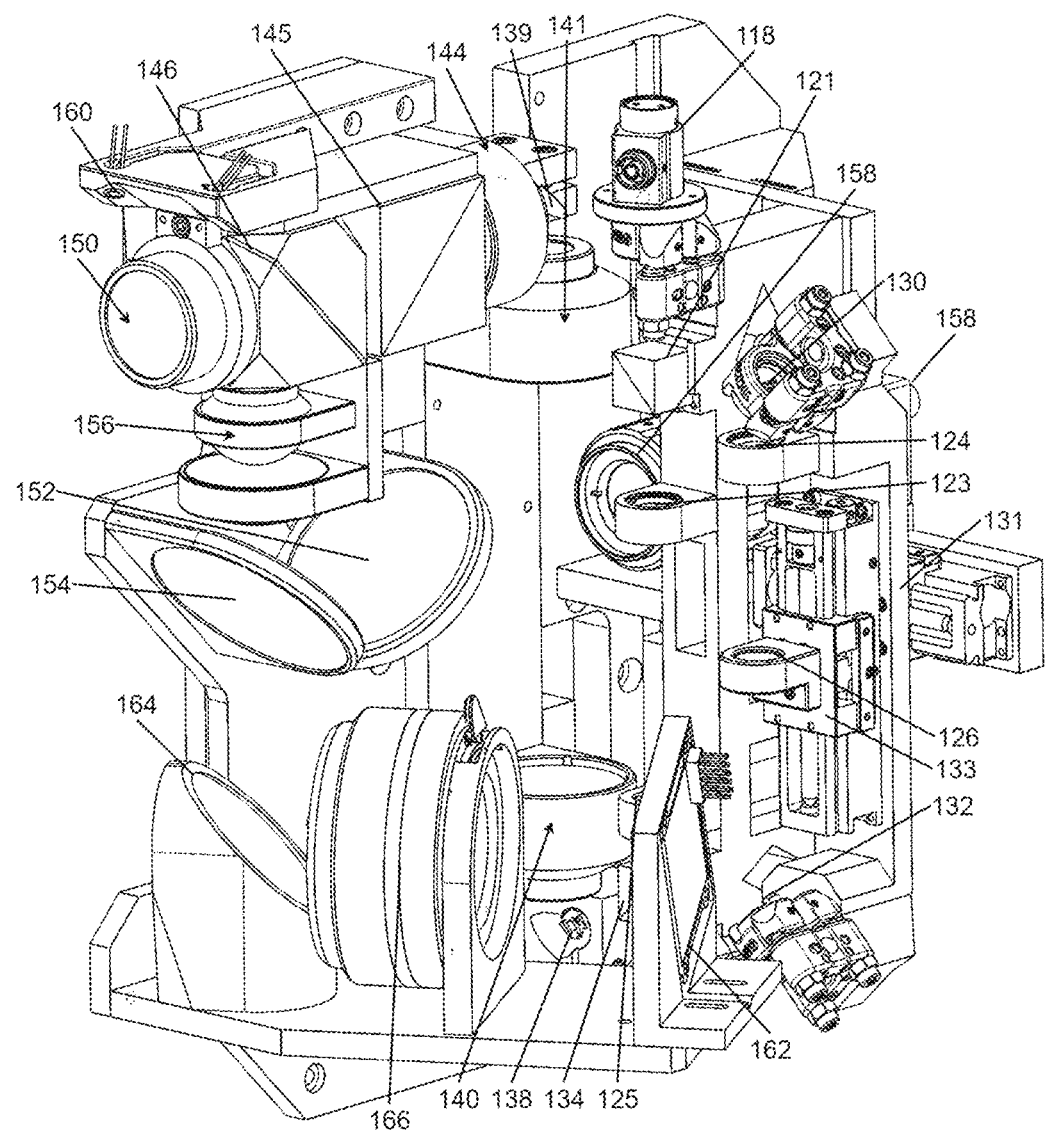
FIG. 4 is a perspective view of an example OCT system in accordance with embodiments of the present disclosure.

FIG. 4 illustrates a perspective view of an example OCT system in accordance with embodiments of the present disclosure. The OCT system is a tabletop system configured to provide simultaneous imaging of both retina and ocular anterior segment. Referring to FIG. 4, an off-axis parabolic reflective collimator 118 collimates light from an input fiber. Light is split into two linear polarized channels by a polarizing beam splitter cube 121. P-polarized light that passes through the beam splitter goes through a beam shrinking telescope consisting of achromatic lenses 123 and 125. After the telescope, they transmit through another polarizing beam splitter cube 134. S-polarized light that is reflected by cube 121 proceeds to fold mirror 130. Light is reflected by mirror 130 to a beam expanding telescope consisting of two achromatic lenses 124 and 126. Lens 126 can be moved by a micro translation stage 133 to provide retinal diopter control separately from the anterior segment imaging path. A second fold mirror 132 returns light to polarizing beam splitter cube 134. By placing mirrors 130 and 132, lenses 124 and 126, and micro-translational stage 133 on a second micro-translational stage 131, subject eye length compensation may be achieved separately from the anterior segment imaging path. Following cube 134, both P- and S-polarized light are now coaxial. A fold mirror (not seen in the view given by FIG. 4) reflects light to a galvonometric scanning mirror 138. Lateral scanning can be performed utilizing a pair of separated galvanometers 138 and 139 that are imaged on to one another via a 4-F telescope consisting of lens groups 140 and 141 to provide a low distortion image plane for future quantitative morphology measurements. The orientation of 138 and 139 is such that it rotates light leaving 134 where P-polarized light is rotated to be S-polarized light and S-polarized light is rotated to be P-polarized. Light leaves the second scanning mirror 139 to lens group 144 which creates a telecentric image plane at its back focal plane. Light leaves the lens group and enters polarizing beam splitter 145 where P-polarized light is transmitted through to a custom wire grid polarizing beam splitter cube 146. This light transmits through cube 146 and is collimated by lens group 150. After leaving lens group 150 the, P-polarized light would be imaged on to the subject's retina through the use of the subject's ocular optics. S-polarized light is reflected by cube 145, reflected by fold dichroic mirrors 152 and 154, and is refracted by lens group 156. Lens group 156 forms a 4-F telescope with group 150 by reflecting off the hypotenuse of wire grid polarizing beam splitter cube 146. This telescope images the telecentric focal plane of lens group 144 on to the subject's ocular anterior chamber. By having a larger acceptance angle over conventional polarizing beam splitters, wire grid polarizing cube 146 enables wider angle viewing of the retina and provides a large telecentric scan area on the anterior segment. An integrated fixation target is provided via a software controllable OLED screen 162 and is integrated with the OCT system via a dichroic mirror 154, fold mirror 164, and lens 166. Alignment to the imaging subject's iris is provided through a camera 158 and oblique illumination near-infrared LEDs 160. The camera is integrated into the OCT system by transmitting through dichroic mirror 152 and reflected by dichroic mirror 154.

Figure 5A:
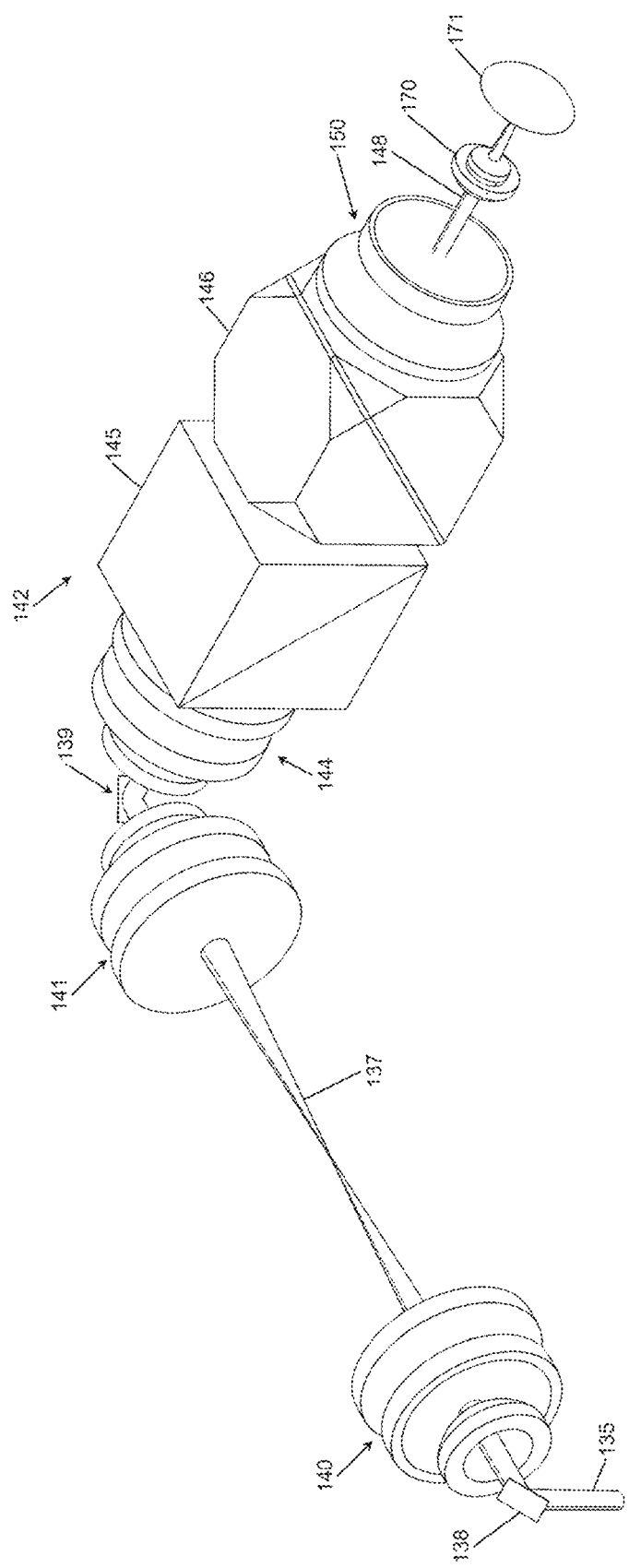
FIGS. 5A and 5B are renderings of imaging optics in accordance with embodiments of the present disclosure.
Figure 5B:
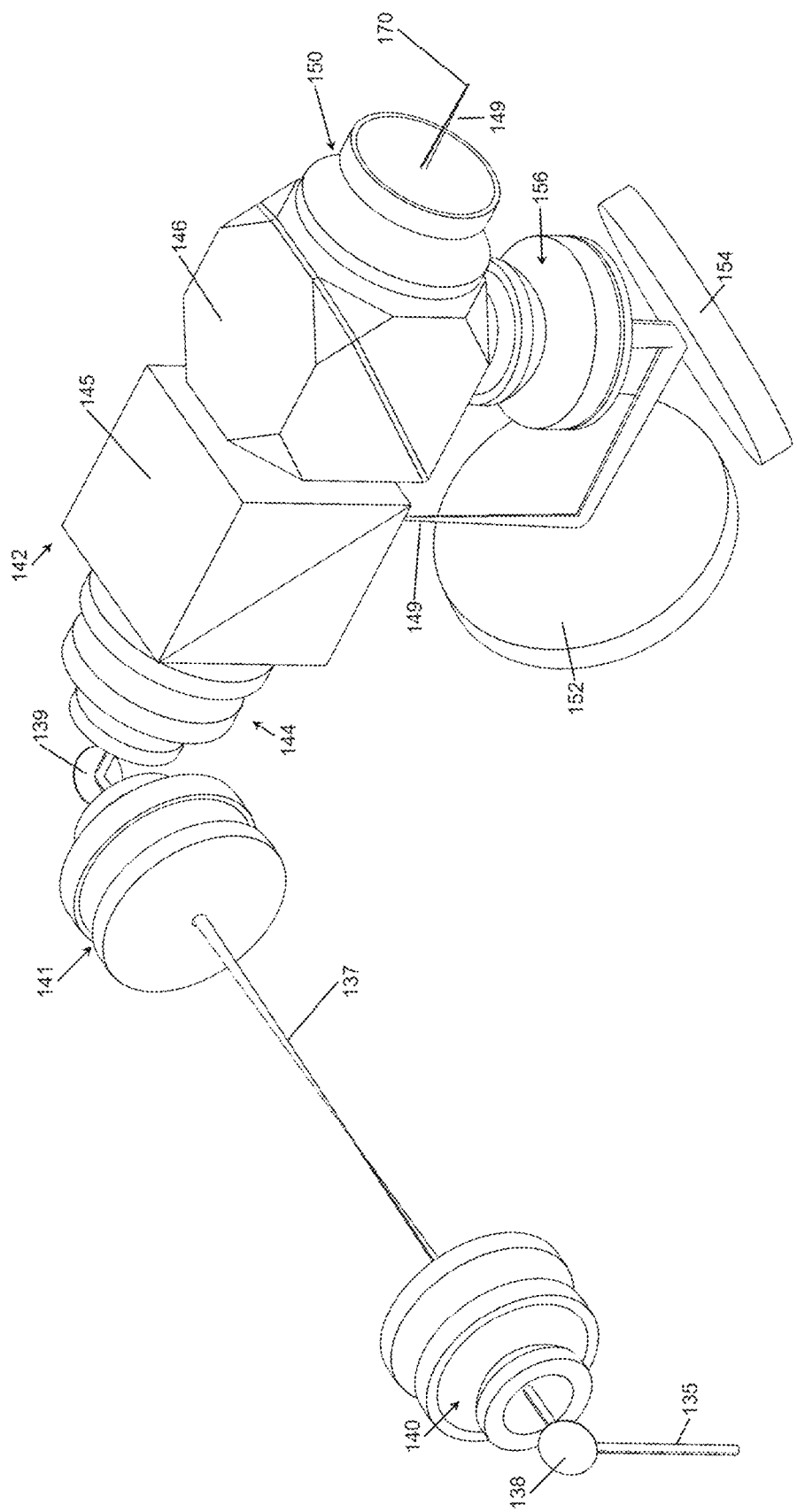

FIGS. 5A and 5B are renderings of imaging optics of an example OCT system in accordance with embodiments of the present disclosure. These renderings were generated by used of the ZEMAX® optical design software available from Zemax LLC. FIG. 5A shows ray tracing of various scan positions within the posterior segment imaging optical system. FIG. 5B shows ray tracing of various scan positions within the anterior segment imaging optical system.

Figure 6:
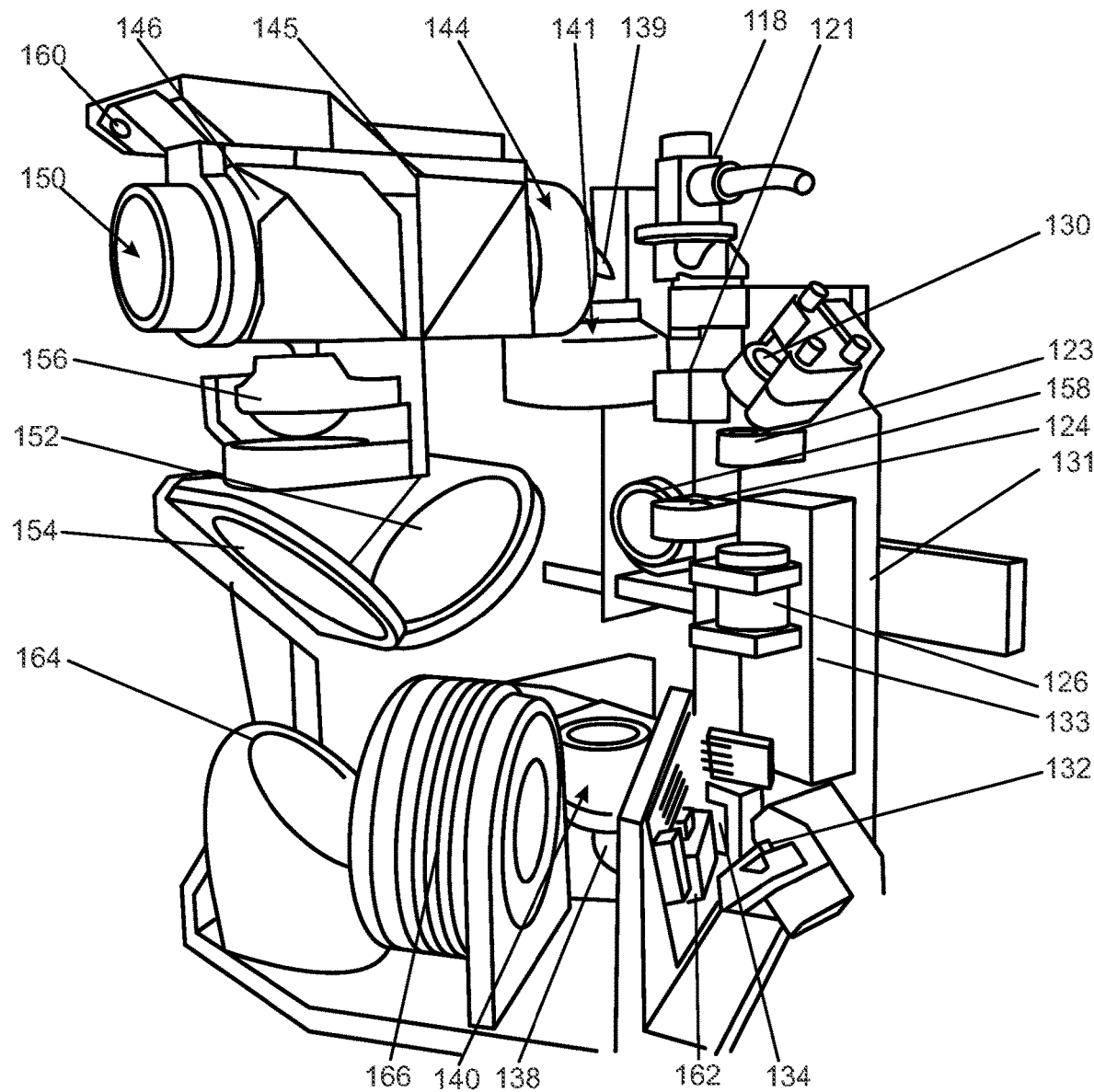
FIG. 6 is a photograph of an example whole eye OCT system in accordance with embodiments of the present disclosure.

FIG. 6 is a photograph of an example whole eye OCT system in accordance with embodiments of the present disclosure. The system shown in FIG. 6 is shown on an ophthalmic imaging platform. Referring to FIG. 6, an off-axis parabolic reflective collimator 118 collimates light from an input fiber. Light is split into two linear polarized channels by a polarizing beam splitter cube 121. P-polarized light that passes through the beam splitter goes through a beam shrinking telescope consisting of achromatic lens 123 and second achromatic lens not visible within the image. After the telescope, they transmit through another polarizing beam splitter cube 134. S-polarized light that is reflected by cube 121 proceeds to fold mirror 130. Light is reflected by mirror 130 to a beam expanding telescope consisting of two achromatic lenses 124 and 126. Lens 126 can be moved by a micro translation stage 133 to provide retinal diopter control separately from the anterior segment imaging path. A second fold mirror 132 returns light to polarizing beam splitter cube 134. By placing mirrors 130 and 132, lenses 124 and 126, and micro-translational stage 133 on a second micro-translational stage 131, subject eye length compensation may be achieved separately from the anterior segment imaging path. Following cube 134, both P- and S-polarized light are now coaxial. A fold mirror (not seen in the view given by FIG. 6) reflects light to a galvonometric scanning mirror 138. Lateral scanning can be performed utilizing a pair of separated galvanometers 138 and 139 that are imaged on to one another via a 4-F telescope consisting of lens groups 140 and 141 to provide a low distortion image plane for future quantitative morphology measurements. The orientation of 138 and 139 is such that it rotates light leaving 134 where P-polarized light is rotated to be S-polarized light and S-polarized light is rotated to be P-polarized. Light leaves the second scanning mirror 139 to lens group 144 which creates a telecentric image plane at its back focal plane. Light leaves the lens group and enters polarizing beam splitter 145 where P-polarized light is transmitted through to a custom wire grid polarizing beam splitter cube 146. This light transmits through cube 146 and is collimated by lens group 150. After leaving lens group 150 the P-polarized light would be imaged on to the subject's retina through the use of the subject's ocular optics. S-polarized light is reflected by cube 145, reflected by fold dichroic mirrors 152 and 154, and is refracted by lens group 156. Lens group 156 forms a 4-F telescope with group 150 by reflecting off the hypotenuse of wire grid polarizing beam splitter cube 146. This telescope images the telecentric focal plane of lens group 144 on to the subject's ocular anterior chamber. By having a larger acceptance angle over conventional polarizing beam splitters, wire grid polarizing cube 146 enables wider angle viewing of the retina and provides a large telecentric scan area on the anterior segment. An integrated fixation target is provided via a software controllable OLED screen 162 and is integrated with the OCT system via a dichroic mirror 154, fold mirror 164, and lens 166. Alignment to the imaging subject's iris is provided through a camera 158 and oblique illumination near-infrared LEDs 160. The camera is integrated into the OCT system by transmitting through dichroic mirror 152 and reflected by dichroic mirror 154.

In accordance with embodiments, sample arms as disclosed herein may be sized to be readily used in an ophthalmic clinic. Material for making OCT systems disclosed herein include, but are not limited to, aircraft aluminum to optimally balance cost, weight, and strength with additional custom components composed of 3D printed plastics.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. An optical coherence tomography (OCT) imaging system comprising:
   a source having an associated source arm path;
   a reference arm coupled to the source arm path;
   a sample arm having an associated sample arm path and coupled to the source arm path, wherein at least two polarizing beam splitters are configured to split and recombine to provide two different imaging channels for simultaneously scanning both an anterior and posterior portion of an eye of a subject; and
   a first lens group and a second lens group, wherein the at least two polarizing beam splitters are positioned between the first lens group and the second lens group.

2. The OCT imaging system of claim 1, wherein the source is a laser.

3. The OCT imaging system of claim 1, wherein the source is a low temporal coherence light source.

4. The OCT imaging system of claim 1, wherein the reference arm has a single arm path.

5. The OCT imaging system of claim 1, wherein the reference arm is polarization encoded.

6. The OCT imaging system of claim 1, further comprising a 4-F telescope positioned along the sample arm path.

7. The OCT imaging system of claim 1, wherein the at least two beam splitters are configured to split light into linear P-polarized and S-polarized light.

8. The OCT imaging system of claim 1, wherein the at least two beam splitters are configured to transmit P-polarized light and to reflect S-polarized light.

9. The OCT imaging system of claim 1, wherein the at least two beam splitters comprise a wire grid polarizer.

10. The OCT imaging system of claim 1, further comprising an alignment system configured to align the eye for scanning.

11. The OCT imaging system of claim 1, further comprising at least one processor and memory configured to generate one or more images of the scanned anterior and posterior portion of the eye.

12. A method for imaging an eye of a subject, the method comprising:
    providing an optical coherence tomography (OCT) imaging system comprising:
       a source having an associated source arm path;
       a reference arm coupled to the source arm;
       a sample arm having an associated sample arm path and coupled to the source arm path, wherein at least two beam splitters are configured to split and recombine to provide two different imaging channels; and a first lens group and a second lens group, wherein the at least two beam splitters are positioned between the first lens group and the second lens group;

using the at least two beam splitters to simultaneously scan both an anterior and posterior portion of an eye of a subject; and generating one or more images based on the scanned anterior and posterior portion of the eye.

13. The method of claim 12, wherein the source is a low temporal coherence light source.

14. The method of claim 12, wherein the reference arm has a single arm path.

15. The method of claim 12, wherein the reference arm is polarization encoded.

16. The method of claim 12, wherein the OCT imaging system further comprises a 4-F telescope positioned along the sample arm path.

17. The method of claim 12, wherein the at least two beam splitters are configured to split light into linear P-polarized and S-polarized light.

18. The method of claim 12, wherein the at least two beam splitters comprise a wire grid polarizer.

* * * * *